(12) United States Patent
Crossman et al.

(10) Patent No.: US 7,066,907 B2
(45) Date of Patent: Jun. 27, 2006

(54) INJECTION DEVICES

(75) Inventors: David Danvers Crossman, Oxford (GB); Jeremy Marshall, Oxford (GB)

(73) Assignee: Owen Mumford Limited, Oxford (GB)

( * ) Notice: Subject to any disclaimer, the term of this patent is extended or adjusted under 35 U.S.C. 154(b) by 148 days.

(21) Appl. No.: 10/319,472

(22) Filed: Dec. 16, 2002

(65) Prior Publication Data

US 2003/0093036 A1 May 15, 2003

Related U.S. Application Data

(63) Continuation of application No. 09/462,366, filed as application No. PCT/GB98/02103 on Jul. 16, 1998, now abandoned.

(30) Foreign Application Priority Data

Jul. 16, 1997 (GB) .............................................. 9714948

(51) Int. Cl.
*A61M 5/00* (2006.01)

(52) U.S. Cl. ....................................... 604/110; 604/197
(58) Field of Classification Search ................ 604/110, 604/131, 135, 232, 134, 218, 197
See application file for complete search history.

(56) References Cited

U.S. PATENT DOCUMENTS

| 3,880,163 A | 4/1975 | Ritterskamp |
| 4,258,713 A | 3/1981 | Wardlaw |
| 5,267,963 A | 12/1993 | Bachynsky |
| 5,599,309 A | 2/1997 | Marshall et al. |
| 6,099,503 A | 8/2000 | Stradella |

FOREIGN PATENT DOCUMENTS

| DE | 20 17 598 | 10/1970 |
| EP | 0 014 006 | 8/1980 |
| EP | 0 516 473 | 12/1992 |
| FR | 2 342 079 | 9/1977 |
| GB | 1 311 937 | 3/1973 |
| WO | 94/11041 | 5/1994 |

*Primary Examiner*—Kevin C. Sirmons
(74) *Attorney, Agent, or Firm*—Young & Thompson

(57) ABSTRACT

A one-shot throwaway injection device has a barrel that houses a syringe initially in a retracted state held back by a trigger against a drive spring. Actuation of the trigger causes the syringe to be thrust forwards by the spring acting on its plunger until the needle is fully projecting, and then the dose is ejected by the final expansion of the spring. Release of the trigger allows a return spring to urge the syringe back and retract the needle. The barrel is a unitary plastics moulding of two longitudinally split halves hinged together with the trigger integrally formed with one of these halves. The other components and the syringe are positioned in one half which is then closed up and fastened to the other half to complete the barrel.

16 Claims, 4 Drawing Sheets

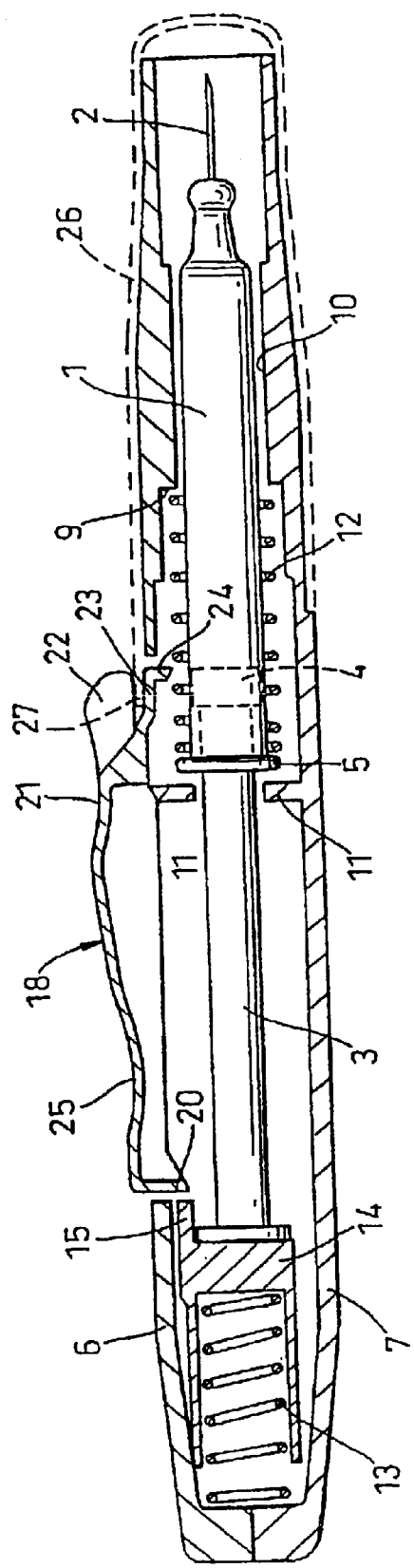
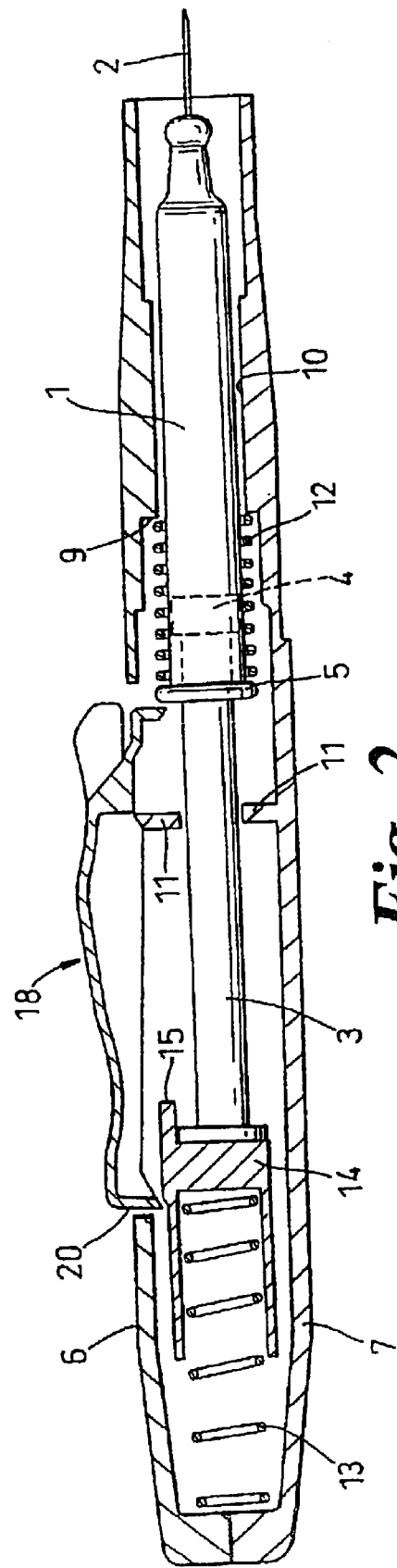
Fig. 1
Fig. 2

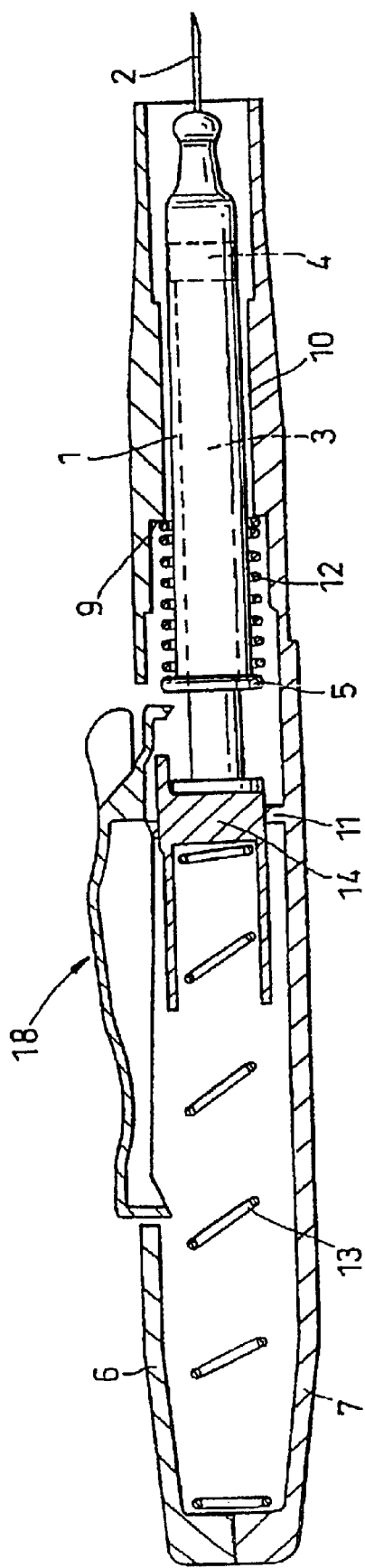
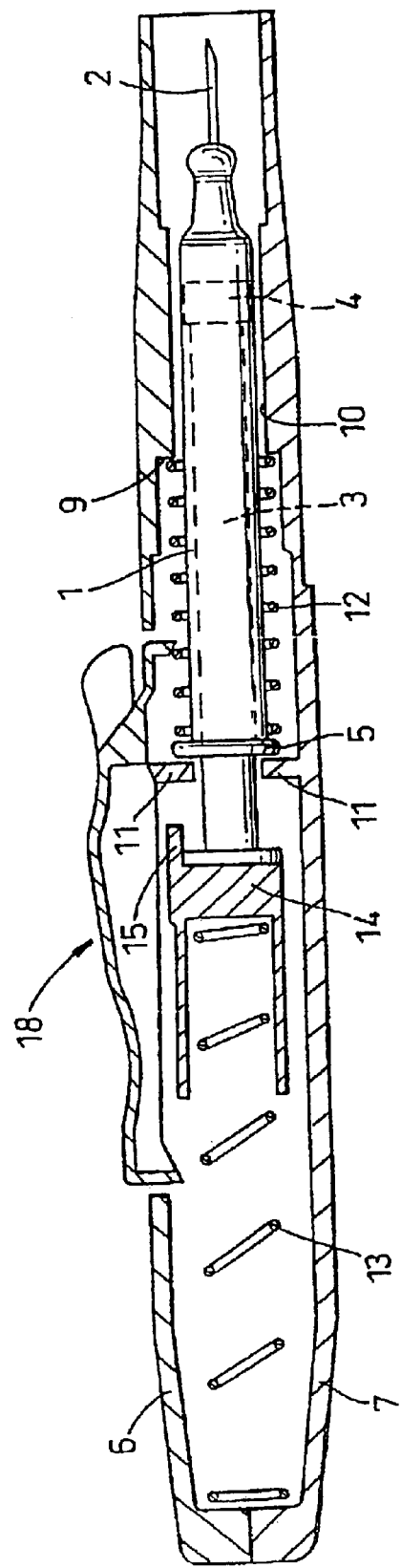
Fig. 3
Fig. 4

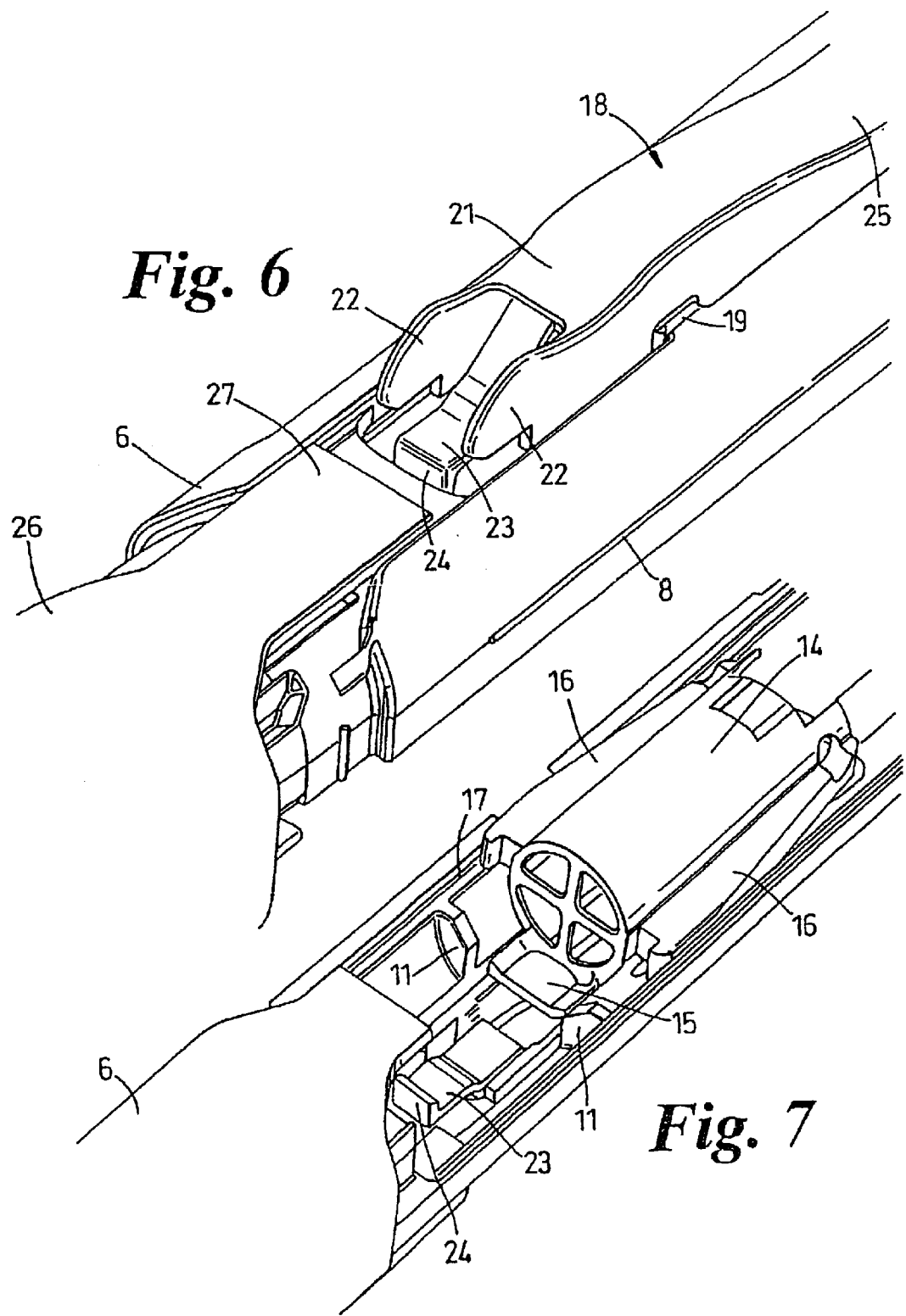

INJECTION DEVICES

This application is a continuation of application Ser. No. 09/462,366, filed on Jan. 7, 2000 now abandoned. Application Ser. No. 09/462,366 is the national phase of PCT International Application No. PCT/GB98/02103 filed on Jul. 16, 1998 under 35 U.S.C. § 371. The entire contents of each of the above-identified applications are hereby incorporated by reference.

BACKGROUND OF THE INVENTION

This invention relates to injection devices.

It concerns devices which are fitted with a syringe having a capsule with a needle projecting from the forward end and a plunger from the rear end. A trigger and spring mechanism, when operated, shoots the syringe forwardly to project the needle, and then continues to act on the plunger to eject the dose. There is also a return spring arrangement to retract the needle after use, thereby making it safe.

Hitherto, these firing devices have been quite complicated and expensive, and it is necessary to load and unload the syringe before and after use and to keep the device itself for repeated use. It is too expensive simply to throw away. Also there have been problems with ensuring that the return spring works properly.

However, unloading particularly has its dangers with a sharp and possibly contaminated needle, and it is the aim of this invention to provide an injection device which is simple and cheap enough to be thrown away with the syringe safely retracted inside it.

SUMMARY OF THE INVENTION

According to one aspect of the present invention there is provided an injector device for containing and operating a syringe having a capsule with a needle projecting from the forward end and a plunger from the rear end, the device having a first spring initially in a compressed energised state at the rear end of the device held by a trigger, and a second spring initially not fully energised and surrounding the capsule, wherein operation of the trigger releases the first spring which first urges the syringe forwardly by acting on the plunger and thence through the dose within the syringe, and secondly, when the syringe reaches a needle projecting position, presses the plunger forwards relative to the capsule to eject the dose, and wherein the second spring, fully compressed by this action, then exerts itself to retract the syringe and its needle, characterised in that the device has an integrally moulded two-part body formed in an open state, the trigger also being part of the integral moulding, and in that the body is closed and secured around a dose filled syringe in the retracted position and the first and second coil springs.

Conveniently, the body is in two substantially semi-cylindrical halves, joined by at least one thin web along adjacent longitudinal edges.

Preferably the trigger is a portion separated from a respective half of the body by all but webs that form a transverse hinge at an intermediate position along the trigger. The rear end of the trigger may have an inward projection that initially maintains the first spring primed, release being by pressing inwardly on the forward end. This forward end may have a pawl to catch behind the capsule when the capsule reaches the needle projecting position, thereby to prevent retraction under the influence of the second spring as long as the forward end remains pressed inwardly or the trigger is operated positively to withdraw the pawl.

The trigger may be duplicated, with one on each half, these triggers being squeezed together to operate the device.

Generally, there will also be a separately moulded protective cap to fit over the forward end of the completed body. This cap is conveniently adapted to co-operate with the trigger to prevent that being operated while the cap is on. The cap can also have an internal formation that projects into the barrel to co-operate with a sheath initially provided over the needle of the capsule, removal of the cap causing the sheath to be pulled off the needle.

The cap may be refitted after use, to be thrown away with the injection device.

According to another aspect of the invention there is provided an injector device for containing and operating a syringe having a capsule with a needle projecting from the forward end and a plunger from the rear end, the device having a first spring initially in a compressed energised state at the rear end of the device held by a trigger, and a second spring initially not fully energised and surrounding the capsule, wherein operation of the trigger releases the first spring which first urges the syringe forwardly by acting on the plunger and thence through the dose within the syringe, and secondly, when the syringe reaches a needle projecting position, presses the plunger forwards relative to the capsule to eject the dose, and wherein the second spring, fully compressed by this action, then exerts itself to retract the syringe and its needle, characterised in that the trigger is adapted to provide an obstruction to the syringe to prevent the retraction thereof as long as the trigger is maintained in its operated state, the retraction requiring release or an alternative operation of the trigger.

BRIEF DESCRIPTION OF THE DRAWINGS

For a better understanding of the invention, one embodiment will now be described, by way of example, with reference to the accompanying drawings, in which:

FIGS. 1–4 are simplified axial sections of an injection device in various stages from initial assembly, through use to being ready for disposal, FIG. 6 is a perspective view of part of the device showing a trigger in more detail, and FIG. 7 is a perspective view of part of the device, with half of the barrel removed, showing a drive member and part of the inside of the trigger.

DESCRIPTION OF THE PREFERRED EMBODIMENTS

Figure 5:
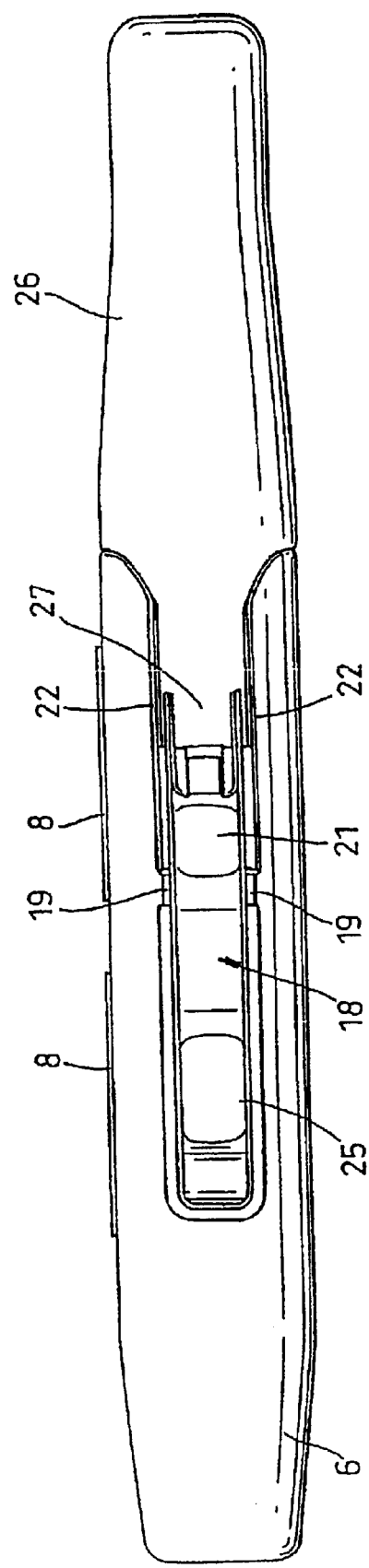
FIG. 5 is a plan view of the injection device.

The injection device is designed to contain and operate a syringe having a capsule 1, a needle 2 at its forward end, and a plunger 3 at its rearward end which can actuate a piston 4 within the capsule to eject a dose through the needle 2. The rear end of the capsule has an outwardly projecting rim 5. This syringe is of known form.

The body of the injection device is formed by two generally semi-cylindrical halves 6 and 7 brought together and secured by adhesive or welding for example, or by snap-fitting lugs and sockets, to make a barrel with tapers at each end. The halves 6 and 7 are moulded in one piece in an opened-out condition, being joined by a single long web, or several shorter webs 8. These extend along one pair of adjacent longitudinal edges of the halves 6 and 7 between the tapering ends, and serve as hinges when the halves are closed together.

Towards its forward end the body reduces internally at a shoulder 9 to a passage 10 which serves as a longitudinal guide for the capsule 1. At about the mid-length, there are internal ribs 11 non-obstructive to the piston 4 and the member described below which drives it but which form an abutment for the rim 5. A coil spring 12, initially only partially compressed, surrounds the capsule to act between the shoulder 9 and the out-turned rim 5. The forward end of the barrel is open for passage of the needle 2.

At the rear end the barrel is closed and provides a seat for another coil spring 13, initially compressed and nesting in the rearward facing cup of a slider 14 forming a drive member. The forward end of this slider bears against the rear end of the piston 4 and it has a finger 15 projecting forwardly to one side of that rear end and outside the cylindrical envelope of the spring 13. The slider 14 is prevented from rotating by wings 16 which run in internal grooves 17 along the barrel, these grooves being formed by rebates inside the edges of the halves 6 and 7 coming together when the device is closed up.

The half 6 of the barrel is formed with a trigger 18 of generally rectangular form extending lengthwise of the barrel. It is separated from the half 6 around most of its periphery except for two short webs 19 at opposite sides in the region of the ribs 11. These webs form a transverse hinge, the plastics material of which the barrel is moulded allowing a certain flexible resilience. The rear end of the trigger 18 has one part, such as inwardly projecting abutment 20, against which the finger 15 initially bears. At the leading end of each trigger, as best seen in FIG. 6, there is a finger pad 21 proud of the barrel, forward of which are two undercut parallel wings 22. Between these wings, and stepped down to the envelope of the barrel, there is a second part, such as pawl 23 with a tooth 24 projecting inwardly at its forward end. The second part can hinge about its rear end by virtue of the plastics construction. Another finger pad 25 is provided towards the rear of the trigger.

As supplied, this injection device has a cap 26 which fits closely over the forward portion of the barrel, as shown in outline in FIG. 1. It has a rearward extension 27 to engage the undercuts below the wings 22 and over the back of the pawl 23. It is illustrated approaching this position in FIG. 6. At the forward end, the cap may have an internal formation which extends inside the barrel and which engages behind the base of a needle sheath (not shown) in known manner.

In the FIG. 1 position, the injector is inoperative, the trigger 18 being held against actuation by the extension 27 of the cap 26. The spring 12 is partially compressed and semi energised, and the spring 13 is fully compressed and therefore fully energised. When the device is to be used, the cap is pulled off, this simultaneously freeing the trigger and removing the sheath.

The device is then applied against the skin of the patient and the finger pad 21 is pressed in as shown in FIG. 2. This hinges the trigger 18 so that the abutment 20 is moved outwardly, clear of the finger 15, thus freeing the compressed spring 13. This expands and, through the slider 14 and the plunger 3, thrusts the syringe forwards.

The trigger action depresses the pawl 23 towards the syringe, where the tooth 24 might interfere with the spring 11. However, because of its flexibility, the pawl bends outwards and snaps over the rearward turns of the spring 12 and the rim 5. The spring 12 is slightly stiffer than the spring 13 over the intermediate and final parts of the latter's expansion, in order to ensure the return of the syringe, but the momentum of the forward thrust ensures that the spring 12 is fully compressed.

When that is achieved, the capsule 1 is arrested and the pawl 23 snaps back into alignment with the trigger for the tooth 24 to engage behind the rim 5 as shown in FIGS. 2 and 3. It may be long enough to remain engaged if the trigger 18 is released, or it may be short, requiring the finger pad 21 to be held down. In any event, the needle 2 is now fully projected, but the spring 13, no longer opposed by the spring 12, continues to expand and the plunger 3 presses the piston 4 forwards, ejecting the dose.

The device is then withdrawn from the patient and the finger pad 21 released if the device is a short tooth version. The trigger 18 springs back to its initial position, the pawl 23 releasing from the rim 5. With a long tooth version, the user presses on the rear finger pad 25 to tilt the trigger back and release the pawl. The spring 12 can now exert itself and push the syringe back, retracting the needle 2 to the position of FIG. 4. The cap 26 may then be refitted, and the device thrown away.

There is a risk that, when pulling off the cap 26, the user will hold the barrel in a manner that will squeeze the finger pad 21, thereby prematurely firing the device. To prevent this, the rim of the cap and the trigger may be so configured that pressure on the finger pad will prevent release of the cap. For example, the end of the extension 27 may be slightly out-turned and the undercuts of the wings 22 notched to receive the out-turned end. The user will, therefore, have to grip the barrel clear of the trigger, allowing the cap to snap free.

It will be understood that the barrel can have one or more windows, particularly in the forward part in order that the state and position of the syringe can be visually checked.

What is claimed:

1. An injector device for containing and operating a syringe having an elongate dose-containing capsule (1) with a needle (2) projecting from a forward end thereof and a plunger (3) from a rear end thereof, the device comprising:

a first spring (13) initially in a compressed energized state at a rear end of the device held by a trigger (18), and a second spring (12) initially not fully energized and surrounding the capsule (1), wherein operation of the trigger (18) releases the first spring (13) which first expands and moves the syringe forwardly and secondly, when the syringe reaches a needle projecting position, moves the plunger (13) forwards relative to the capsule (1) to eject the dose, wherein the second spring (12), fully compressed by this action, then exerts itself to retract the syringe and its needle, and wherein the device has an integrally moulded two-part body (6, 7) formed in an open state, the trigger (18) also being part of the integral moulding, and in that the body is closed and secured around a dose filled syringe in the retracted position and the first and second coil springs (13, 12).

2. An injection device as claimed in claim 1, wherein the body is in two substantially semi-cylindrical halves (6, 7), joined by at least one thin web (8) along adjacent longitudinal edges.

3. An injection device as claimed in claim 1, wherein a forward end of the trigger (18) has a pawl (23) to catch behind the capsule (1) when the capsule reaches the needle projecting position, thereby to prevent retraction under the influence of the second spring (12) as long as the forward end remains pressed inwardly or the trigger is operated positively to withdraw the pawl.

4. An injection device as claimed in claim 1, and further comprising a separately moulded protective cap (26) to fit over the forward end of the completed body.

5. An injection device as claimed in claim 4, wherein the cap (26) when fitted over the forward end of the completed body prevents the trigger (18) from being operated.

6. An injection device as claimed in claim 4, wherein the cap has an internal formation that projects into the barrel to co-operate with a sheath initially provided over the needle of the capsule, removal of the cap causing the sheath to be pulled off the needle.

7. An injector device for containing and operating a syringe having an elongate dose-containing capsule (1) with a needle (2) projecting from a forward end thereof and a plunger (3) from a rear end thereof, the device comprising:

a barrel (6, 7) containing the syringe and providing guidance therefor between a first, rearward position with the needle (2) within the barrel and a second, forward position with the needle (2) projecting from a forward end of the barrel;

an initially compressed first spring (13) within the rear end portion of the barrel (6, 7);

a second spring (12) within the barrel, surrounding the capsule (1) and arranged to act between the barrel (6, 7) and the capsule (1); and a trigger (18) on the barrel for expanding the first spring (13) to move the syringe from said first to said second position and also thereafter for releasing the second spring (12) to reverse that movement and cause the needle (2) to retract into the barrel, wherein the first spring (13) acts between the rear end of the barrel and the plunger (3) and is initially maintained compressed by one part (20) of the trigger (18), wherein the second spring (12) initially holds the capsule (1) in said first position, wherein when the trigger (18) has been operated to expand the first spring (13) and the syringe has been moved forwards thereby to compress the second spring (12) and project the needle (2) from the barrel (6, 7), a second part (23, 24) of the trigger (18) co-operates with the capsule (1) to hold the syringe in said second position against the second spring (12), the first spring (13) then expanding farther and completing the injection by its forward thrust on the plunger (3), and wherein a second, different operation of the trigger (18) releases said second part (23, 24) from the capsule (1), allowing the second spring (12) to urge the capsule (1) rearwardly, overcoming the de-energized first spring (13), to retract the needle (2) within the barrel (6, 7).

8. An injection device as claimed in claim 7, wherein operation of the trigger (18) to release said one part (20) from the first spring (13) moves the second part (23, 24) into position to hold the syringe in the forward position.

9. An injection device as claimed in claim 8, wherein release of the trigger (18) after said operation removes said second part (23, 24) out of its position holding the syringe.

10. An injection device as claimed in claim 8, wherein release of the trigger (18) after said operation leave said second part (23, 24) holding the syringe in its forward position, and in that the trigger (18) requires operation reverse to that of the first operation to release the syringe for rearward movement.

11. An injection device as claimed in claim 1, wherein the trigger is aligned lengthwise of the device, and further comprising webs connecting the trigger to one part of the body at an intermediate position of the trigger and acting as a pivot.

12. An injection device as claimed in claim 1, wherein a rear end of the trigger has an inwardly projecting abutment which is initially engaged by the first spring and which thereby keeps the first spring in its compressed energized state until a forward end of the trigger is pressed inwards, this rocking the trigger to release the abutment from the first spring.

13. An injector device for containing a syringe having a capsule with a needle at one end and a movable plunger at an opposite end that ejects a dose from the capsule through the needle, the injector device comprising:

a first semicylindrical half body;

a second semicylindrical half body that is joined to said first half body with a hinge, said first and second half bodies forming a generally cylindrical barrel when folded together, said barrel providing a space for the syringe;

a first spring in said barrel that engages the plunger when the syringe is in said barrel;

a second spring in said barrel that surrounds the capsule when the syringe is in said barrel; and a trigger having a pawl and a finger pad that pivot about a support on an exterior of said first body half, said trigger being arranged and adapted to release said first spring when said pawl is pressed and to release said second spring when said finger pad is pressed, whereby the needle emerges from said barrel and the plunger depressed when said first spring is released and the needle withdraws into said barrel when said second spring is released.

14. The injector device of claim 13, wherein said finger pad comprises an inward projection that restrains said first spring until said pawl is pressed.

15. The injector device of claim 13, wherein said pawl prevents release of said second spring until said finger pad is pressed.

16. The injector device of claim 13, further comprising a cap that covers an end of said barrel from which the needle emerges, said cap comprising a safety member that prevents pressing of said pawl.

* * * * *